US00PP19641P2

(12) United States Plant Patent
Larsen

(10) Patent No.: US PP19,641 P2
(45) Date of Patent: Jan. 20, 2009

(54) ***OSTEOSPERMUM* PLANT NAMED 'SUNNY CHRISTIAN'**

(50) Latin Name: *Osteospermum ecklonis*
Varietal Denomination: Sunny Christian

(75) Inventor: Bjarne Nyholm Larsen, Odense N. (DK)

(73) Assignee: Sunny Gronnegyden APS, Odense (DK)

( * ) Notice: Subject to any disclaimer, the term of this patent is extended or adjusted under 35 U.S.C. 154(b) by 0 days.

(21) Appl. No.: 11/983,730

(22) Filed: Nov. 12, 2007

(51) Int. Cl.
*A01H 5/00* (2006.01)

(52) U.S. Cl. ..... Plt./360
(58) Field of Classification Search ..... Plt./360
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Osteospermum* plant named 'Sunny Christian', characterized by its compact and mounded plant habit; freely branching growth habit; freely flowering habit; daisy-type inflorescences with oblanceolate-shaped ray florets that are blush white in color with light brown and brown-striped lower surfaces; and have good garden performance.

1 Drawing Sheet

Botanical designation: *Osteospermum ecklonis.*
Cultivar denomination: 'Sunny Christian'.

BACKGROUND OF THE INVENTION

The present invention relates to a new and distinct cultivar of *Osteospermum* plant, botanically known as *Osteospermum ecklonis,* and hereinafter referred to by the name 'Sunny Christian'.

The new *Osteospermum* is a product of a planned breeding program conducted by the Inventor in Odense, Denmark. The objective of the program is to create and develop new *Osteospermum* cultivars with compact and uniformly mounded plant habit, freely flowering habit and attractive inflorescence coloration.

The new *Osteospermum* originated from a cross-pollination by the Inventor in May, 2004 of a proprietary selection of *Osteospermum ecklonis* identified as code number 10.501.02, not patented, as the female, or seed, parent with the *Osteospermum ecklonis* cultivar Sunny Serena, disclosed in U.S. Plant Pat. No. 15,693, as the male, or pollen, parent. The new *Osteospermum* was discovered and selected by the Inventor as a single flowering plant within the progeny of the stated cross-pollination in a controlled environment in Odense, Denmark in June, 2005.

Asexual reproduction of the new *Osteospermum* by terminal cuttings in a controlled environment in Odense, Denmark since January, 2007, has shown that the unique features of this new *Osteospermum* are stable and reproduced true to type in successive generations.

SUMMARY OF THE INVENTION

The cultivar Sunny Christian has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunny Christian'. These characteristics in combination distinguish 'Sunny Christian' as a new and distinct cultivar of *Osteospermum:*

1. Compact and mounded plant habit.
2. Freely branching growth habit.
3. Freely flowering habit.
4. Daisy-type inflorescences with oblanceolate-shaped ray florets that are blush white in color with light brown and brown-striped lower surfaces.
5. Good garden performance.

Plants of the new *Osteospermum* differ from plants of the female parent selection in the following characteristics:

1. Upper surfaces of ray florets of plants of the new *Osteospermum* are blush white in color whereas upper surfaces of ray florets of plants of the female parent selection are white in color.
2. Lower surfaces of ray florets of plants of the new *Osteospermum* are light brown and brown-striped whereas lower surfaces of ray florets of plants of the female parent selection are bright yellow in color.

Plants of the new *Osteospermum* differ from plants of the male parent, the cultivar Sunny Serena, in the following characteristics:

1. Upper surfaces of ray florets of plants of the new *Osteospermum* are blush white in color whereas upper surfaces of ray florets of plants of the cultivar Sunny Serena are salmon in color.
2. Lower surfaces of ray florets of plants of the new *Osteospermum* are light brown and brown-striped whereas lower surfaces of ray florets of plants of the cultivar Sunny Serena are brownish salmon in color.

Plants of the new *Osteospermum* can be compared to plants of the *Osteospermum* cultivar Sunny Henry, disclosed in U.S. Plant Pat. No. 16,251. In side-by-side comparisons conducted in Odense, Denmark, plants of the new

*Osteospermum* differed from plants of the cultivar Sunny Henry primarily in the lower surface color of the ray florets as lower surfaces of ray florets of plants of the cultivar Sunny Henry were bright yellow in color. In addition, plants of the new *Osteospermum* had larger inflorescences than plants of the cultivar Sunny Henry.

BRIEF DESCRIPTION OF THE PHOTOGRAPHS

The accompanying photographs illustrate the overall appearance of the new *Osteospermum*. This photographs shows the colors as true as it is reasonably possible to obtain in colored reproductions of this type. Colors in the photographs may differ slightly from the color values cited in the detailed botanical description which accurately describe the colors of the new *Osteospermum*.

The photograph at the top of the sheet comprises a side perspective view of a typical flowering plant of 'Sunny Christian'.

The photograph at the bottom of the sheet is a close-up view of a typical inflorescence of 'Sunny Christian'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in Odense, Denmark during the spring in a glass-covered greenhouse and under conditions and practices which approximate those generally used in commercial *Osteospermum* production. During the production of the plants, day temperatures ranged from 14° C. to 20° C., night temperatures averaged 14° C. and light levels ranged from 200 to 800 watts per square meter. Measurements and numerical values represent averages for typical flowering plants. Plants were pinched one time and were about 15 weeks old when the photographs and description were taken.

Botanical classification: *Osteospermum ecklonis* cultivar Sunny Christian.

Parentage:

*Female, or seed, parent.*—Proprietary selection of *Osteospermum ecklonis* identified as code number 10.501.02, not patented.

*Male, or pollen, parent.*—*Osteospermum ecklonis* cultivar Sunny Serena, disclosed in U.S. Plant Pat. No. 15,693.

Propagation:

*Type.*—Terminal vegetative cuttings.

*Time to initiate roots, summer.*—About ten days at 18° C.

*Time to initiate roots, winter.*—About twelve days at 18° C. to 20° C.

*Time to produce a rooted cutting, summer.*—About three weeks at 18° C. to 20° C.

*Time to produce a rooted cutting, winter.*—About four weeks at 18° C.

*Root description.*—Medium in thickness, fibrous; white in color.

*Rooting habit.*—Freely branching; moderately dense.

Plant description:

*Plant form/growth habit.*—Compact and mounded plant habit. Inflorescences positioned above and beyond the foliar plane. Low to moderately vigorous growth habit.

*Plant height.*—About 16.3 cm.

*Plant diameter.*—About 23.2 cm.

*Lateral branches.*—Quantity per plant: Freely branching, about 14 lateral branches develop per plant. Length: About 7.4 cm. Diameter: About 4 mm. Internode length: About 1.3 cm. Strength: Strong. Texture: Smooth, glabrous. Color: 144A occasionally flushed with 174A.

*Foliage description.*—Arrangement: Alternate, simple; sessile. Length: About 5.1 cm. Width: About 2.2 cm. Shape: Obovate. Apex: Broadly acute. Base: Cuneate. Margin: Dentate; coarse, irregular. Texture, upper and lower surface: Smooth, glabrous; leathery; moderately dense pubescence along the leaf margins. Venation pattern: Pinnate. Color: Developing foliage, upper surface: Between 137A and 141A. Developing foliage, lower surface: Between 144A and 147A. Fully expanded foliage, upper surface: Slightly darker than between 137A and 147A; venation, 144B. Fully expanded foliage, lower surface: 137C; venation, 143C.

Inflorescence description:

*Appearance.*—Daisy-type inflorescence form with oblanceolate-shaped ray florets. Inflorescences positioned above and beyond the foliage; inflorescences terminal and axillary. Disc and ray florets developing acropetally on a capitulum. Inflorescences face mostly upright to outward. Freely flowering habit; about 42 inflorescences develop per plant. Inflorescences not persistent. Inflorescences faintly fragrant.

*Flowering response.*—In northern Europe, plants of the new *Osteospermum* flower continuously from spring to late summer. Early flowering habit, plants begin flowering about eight weeks after pinching. Inflorescences last about two weeks on the plant.

*Inflorescence bud.*—Height: About 1.2 cm. Diameter: About 9 mm. Shape: Broadly elliptic. Color: 137B.

*Inflorescence size.*—Diameter: About 5.8 cm. Depth (height): About 1.8 cm. Disc diameter: About 5 mm. Receptacle diameter: About 9 mm. Receptacle height: About 4 mm.

*Ray florets.*—Length: About 2.8 cm. Width: About 8 mm. Shape: Oblanceolate. Apex: Retuse. Base: Attenuate. Margin: Entire. Texture: Smooth, glabrous; at the base, pubescent. Number of ray florets per inflorescence: About 21 in about two whorls. Color: When opening, upper surface: Close to between 155D and N155B; towards the apex, lightly blushed with 71A. When opening, lower surface: 182D and 184B stripes. Fully opened, upper surface: Close to between 155D and N155B; towards the apex, lightly blushed with 71A. Fully opened, lower surface: 164B to 164C and 176B stripes.

*Disc florets.*—Shape: Tubular; apex dentate, five-pointed. Length: About 9 mm. Diameter, apex: About 2 mm. Diameter, base: About 0.9 mm. Number of disc florets per inflorescence: About 110. Color: Immature: Close to 160A to 160B; towards the apex, 13C. Mature: Between 150D and 160D.

*Phyllaries.*—Quantity per inflorescence: About 20 in a single whorl. Length: About 9 mm. Width: About 1.5 mm. Shape: Lanceolate. Apex: Acuminate, elongated. Base: Cuneate. Margin: Entire. Texture, upper and lower surfaces: Sparsely pubescent. Color, upper surface: 143A. Color, lower surface: 143C.

*Peduncles.*—Length, terminal peduncle: About 8.2 cm. Diameter: About 2 mm. Strength: Strong. Aspect, terminal peduncles: Mostly upright. Aspect, axillary peduncles: About 30° from vertical. Texture: Sparsely pubescent. Color: 144A.

*Reproductive organs.*—Androecium: Present on disc florets only. Anther shape: Lanceolate. Anther length: About 2 mm. Anther color: Close to 200A. Pollen amount: Scarce. Pollen color: 21A. Gynoecium: Present on both ray and disc florets. Pistil length: About 5 mm. Stigma shape: Lanceolate. Stigma color: 163A. Style length: About 1 mm. Style color: 25B to 25C. Ovary color: 145D.

*Seeds/fruits.*—Seed and fruit development have not been observed on plants of the new *Osteospermum.*

Disease/pest resistance: Plants of the new *Osteospermum* have not been shown to be resistant to pathogens and pests common to *Osteospermums.*

Garden performance: Plants of the new *Osteospermum* have been observed to have good garden performance and to tolerate rain, wind and temperatures ranging from about 0° C. to about 40° C.

It is claimed:

1. A new and distinct *Osteospermum* plant named 'Sunny Christian' as illustrated and described.

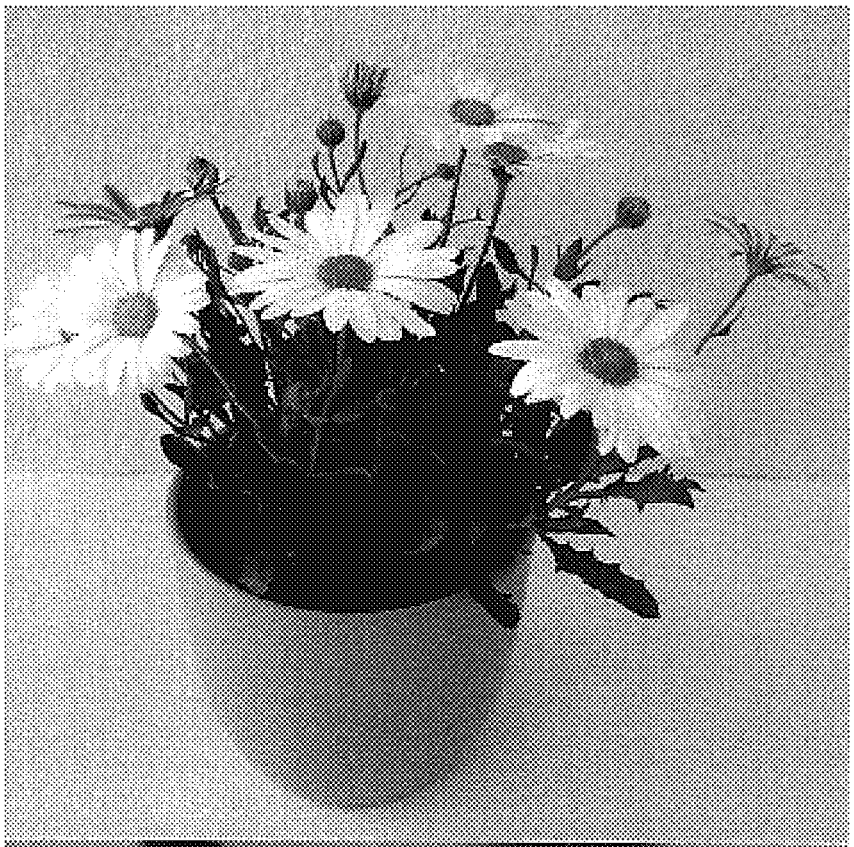
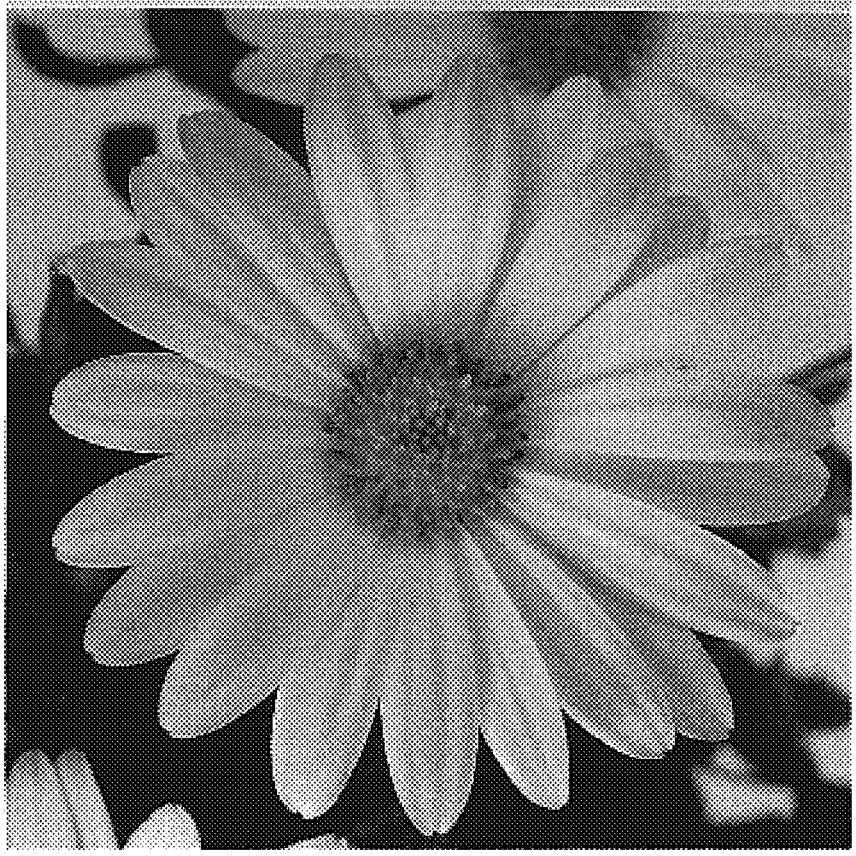

* * * * *